United States Patent
King et al.

(10) Patent No.: US 7,320,346 B2
(45) Date of Patent: Jan. 22, 2008

(54) METHOD OF PROOF TESTING GLASS

(75) Inventors: Toby King, Palo Alto, CA (US); Paul Stuart Bridges, Menlo Park, CA (US); Oliver Shergold, Cottenham (GB)

(73) Assignee: Zogenix, Inc., Emeryville, CA (US)

( * ) Notice: Subject to any disclaimer, the term of this patent is extended or adjusted under 35 U.S.C. 154(b) by 0 days.

(21) Appl. No.: 11/743,055

(22) Filed: May 1, 2007

(65) Prior Publication Data

US 2007/0193338 A1    Aug. 23, 2007

Related U.S. Application Data

(63) Continuation of application No. 10/539,964, filed as application No. PCT/US03/40587 on Dec. 18, 2003, now Pat. No. 7,231,945.

(30) Foreign Application Priority Data

Dec. 18, 2002    (GB)    ................................. 0229447.8

(51) Int. Cl.
*B65B 1/04*    (2006.01)

(52) U.S. Cl. .................................. 141/83; 73/37; 73/52
(58) Field of Classification Search .................. 141/83, 141/67; 73/37, 52
See application file for complete search history.

(56) References Cited

U.S. PATENT DOCUMENTS

| | | | |
|---|---|---|---|
| 2,314,310 A | 3/1943 | Jackson et al. | |
| 3,230,760 A | 1/1966 | Fryer, Jr. | |
| 3,251,218 A | 5/1966 | Russel | |
| 3,955,402 A | 5/1976 | Harvill | |
| 4,291,573 A | 9/1981 | Richter et al. | |
| 4,916,936 A | 4/1990 | Wilson | |
| 7,231,945 B2 * | 6/2007 | King et al. | ................... 141/83 |

* cited by examiner

*Primary Examiner*—Steven O. Douglas
(74) *Attorney, Agent, or Firm*—Karl Bozicevic; Bozicevic, Field & Francis LLP

(57) ABSTRACT

A method of proof testing glass containers is disclosed. The method involves applying pressure to a sealed container in two discrete stages as shown in FIG. 1. In the first stage, the pressure is increased to a peak over at a first rate. In the second stage, the pressure is reduced to zero at a much greater rate.

22 Claims, 2 Drawing Sheets

METHOD OF PROOF TESTING GLASS

This application is a continuation of Ser. No. 10/539,964, filed Mar. 8, 2006 now U.S. Pat. No. 7,231,945, which is the national phase of international patent application Ser. No. PCT/US2003/040587 filed Dec. 18, 2003 (Publication No. WO 23004/056717) which claims the benefit of priority to Great Britain Patent Application No. 0229447.8 filed Dec. 18, 2002 all of which are incorporated herein by reference in their entirety noting that the current application controls to the extent there is any contradiction with any earlier application and to which applications we claim priority.

BACKGROUND OF THE INVENTION

Needle-free injectors are used as an alternative to needle-type hypodermic injectors for delivering liquid drugs and other substances through the skin and into the underlying tissues. The drug is dispensed from a drug capsule having a piston which is driven with sufficient force that the drug is expelled at sufficiently high pressure to pierce the skin. Typically, the drug capsule will comprise a hollow cylindrical chamber narrowing to a discharge orifice at one end, and a piston slidingly and sealingly located at the other. The piston is caused to move towards the orifice to dispense the drug by a ram, powered by a variety of means such as a spring, pressurised gas or pyrotechnic charge. The orifice diameter can vary from about 0.08 mm to about 0.7 mm, according to the application.

The more successful and controllable injectors employ a two-phase injection pressure profile; the first is a short but very high-pressure pulse to puncture the skin and the second is at a lower pressure to dispense the drug through the hole thus formed. Typically, the first pressure pulse will be of around 100 microsecond duration, and have a peak pressure of 300-500 bar, and the second will last for around 200 milliseconds with a pressure of around 100 bar. The duration of the second phase will vary according to the volume to be delivered.

It is highly preferred that the drug capsule is transparent, so that the contents may be checked for accuracy and contamination. This requirement has placed a severe limitation on the types of materials that may be used, because the transparent material must be strong enough to withstand the extremely high pressures, and must not adversely affect the drug. As a consequence, virtually all of the needle-free injectors proposed use a plastic drug capsule, typically made from polycarbonate. However, such materials are generally unsuitable for storing the drug, because they absorb water from the drug, or are permeable to oxygen, or react in some way with the drug. Therefore, drug capsules made from plastics are required to be filled immediately before use, a rather inconvenient procedure, with a risk of inaccurate filling and contamination, and requiring training of the operators.

The only material with a long history of satisfactory drug storage is borosilicate glass, but this is very brittle and hence there have been few injectors with glass capsules. The obvious problem with glass capsules is the potential for particles of glass to be ejected if they burst.

The underlying causes of the weakness of glass capsules are tiny flaws which occur during manufacture, such as scratches and cracks.

The "Intraject" manufactured by Weston Medical Limited is a pre-filled single-use disposable needle-free injector, having one of the very few glass capsules suitable for long-term drug storage. This is a borosilicate drug capsule of up to 1 ml capacity, made to exceedingly close manufacturing specifications, and further improved by ion exchange strengthening. The breakage rate for these capsules is exceptionally low, but it is desirable to reduce this still further.

Several attempts have been made to reduce the breakage rate for these capsules. For example, further layers of material have been added to the capsule to provide increased physical strength (see international patent publication WO96/15821 in the name of Weston Medical Limited). However, this approach increases significantly the manufacturing costs of the capsule. Additionally, to still further reduce the breakage rate visual inspection techniques have been employed. However, visual inspection techniques are limited both due to the flaw-size which can be detected and the inherent difficulty in automation, which in turn leads to increased cost. Therefore, there is still a requirement for further reducing the incidence of breakages in a cost-effective manner.

SUMMARY OF THE INVENTION

According to the invention, there is provided a method of testing the strength of a glass container, comprising pressurising the container, the container failing the test if it breaks, wherein the container is pressurised to be subjected to a pressure profile which in a first stage increases from a starting pressure to a peak pressure at a first average rate of pressure increase, and which in a second stage decreases from the peak pressure to the starting pressure at a second, greater, average rate of pressure decrease.

Accordingly, the present invention provides a testing method which enables glass containers, such as needle-free injector drug capsules, to have reduced rates of glass breakage by subjecting the containers to a two-stage proof test. This test can be fully automated. In the case of glass capsules for needle-free injectors, the capsules which survive the proof test have increased probability of surviving the high pressures that the capsule will be subject to during firing. The capsules which fail the proof test are the capsules that would be likely to have failed during firing. Hence, overall the resultant number of capsules which break during firing will be reduced.

The two-stages of the proof test may consist of first ramping the pressure up to a peak pressure over a time of approximately 40-250 ms, for example 50 ms, and then as quickly as possible reducing the pressure to zero (i.e. atmospheric pressure), ensuring that the dwell time at the peak pressure is kept to a minimum.

The reduction of the pressure to zero may take 0-10 ms, and preferably less than 2 ms.

The capsule is preferably filled with a liquid during the proof test to provide both hydrostatic loading and an accurate simulation of the conditions the capsule will be subject to during firing of the device. The pressure may be applied hydraulically.

BRIEF DESCRIPTION OF THE DRAWINGS

An example of the invention will now be described in detail with reference to the accompanying drawings, in which.

DETAILED DESCRIPTION

Figure 1:
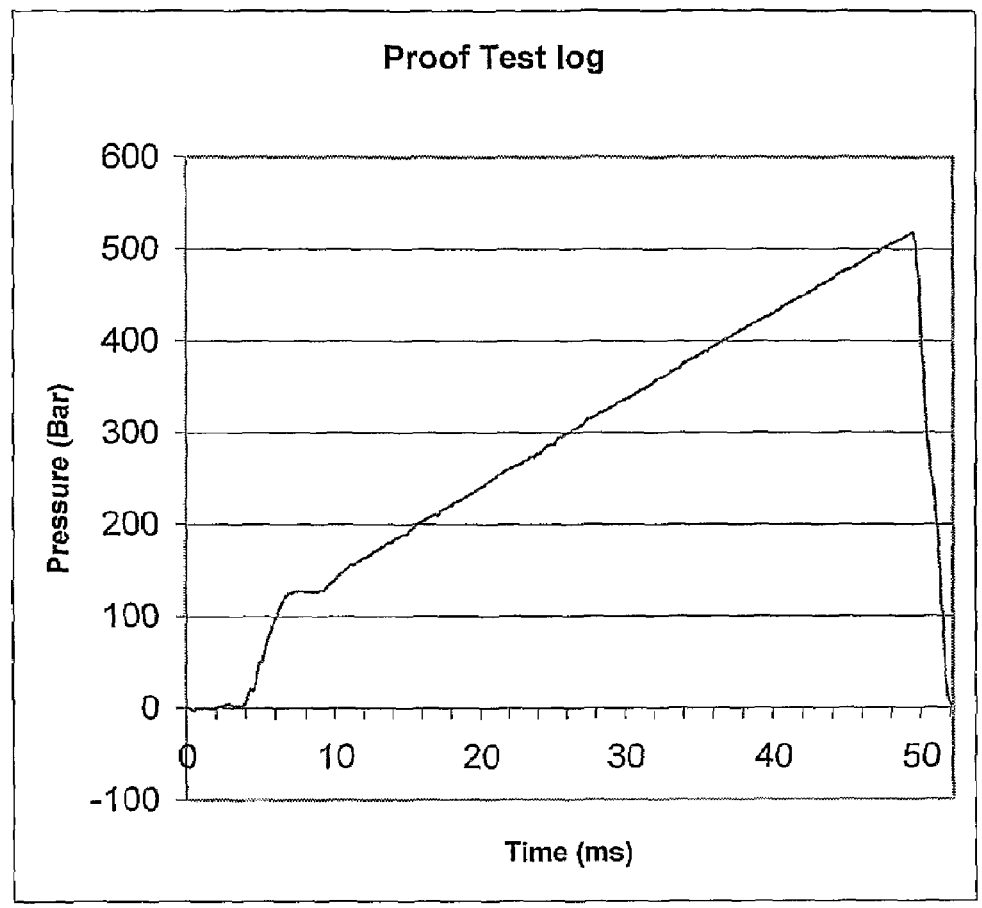
FIG. 1 shows a typical pressure versus time plot for use in the method of the invention.

During the firing cycle of a needle-free injector, the pressures in the capsule rise above 35 MPa. This causes problems for pre-filled needle-free devices, due to drug compatibility requirements—the capsule materials are limited from those which are intrinsically strong, but in which the drug degrades, to borosilicate glasses, which are the industry standard drug storage material, but are prone to catastrophic failure under high stresses.

Borosilicate glasses are not inherently weak. It is the flaws in the glass, generally introduced during manufacturing, which create localised areas of weakness, which, above a stress threshold, lead to rapid crack growth and catastrophic failure. A range of flaws are introduced into the batch, such that some capsules, with the smallest flaw sizes, are strong, whilst others, with the largest flaw sizes, are weak. The consequence of this to needle free injection devices is that a certain percentage of capsules will catastrophically fail during firing.

Glass capsules produced by the Weston manufacturing route have a device failure rate which should be reduced to a minimum. To achieve this, visual inspection techniques are currently used; however, the process is costly. The aim of this invention is to improve on the as-manufactured and visually inspected device failure rate to meet failure rates acceptable to commercial customers in a cost effective manner.

The applicant has found that subjecting a batch of capsules to a two-stage proof test in which the pressure is increased over a time of approximately 50 ms from zero to peak pressures of around 540 bar and then instantaneously reducing the pressure to zero improves the Intraject device failure rate. An example of a suitable pressure time plot from the proof tester developed by Weston Medical is presented in FIG. 1.

Essentially, the pressure profile has a first stage in which the pressure increases from a starting pressure to a peak pressure at a first average rate of pressure increase, and a second stage in which the pressure decreases from the peak pressure to the starting pressure at a second, greater, average rate of pressure decrease.

In this specific example, the duration of the first stage is around 50 ms with a substantially line pressure increase to a peak pressure of 540 Bar, and the second stage has a duration of around 2 ms. The two stages follow each other with no time period during which the peak pressure is maintained.

The proof test works by the following mechanism. Considering first the loading cycle, if, at the precise instant the peak pressure is reached, the statistics of crack growth in a batch of capsules is considered, then all capsules in the batch with any cracks above a particular flaw size, S, will have failed catastrophically. If the pressure is then instantaneously reduced to zero, then to a good approximation, the crack distributions in each capsule will be frozen-in—only the cracks which are moving at a significant speed at the peak pressure will continue to grow. Hence, if there are only a small number of capsules which contain flaws which grow above S after the pressure is reduced to zero, the proof test acts as a near perfect filter, filtering out virtually all capsules with flaw sizes above S. If the pressure is reduced to zero too slowly, there will be a finite time during which flaws in the surviving capsules may continue to grow without catastrophic failure. Consequently, the numbers of capsules in the batch with flaw sizes above S may increase—to the extent that the increase may offset the filtering from the first stage of the proof test.

For needle-free injectors, the purpose of the proof test is to filter out capsules which have cracks above a flaw size, $S_{crit}$—the critical flaw size which would result in catastrophic failure of the device during firing. This will be achieved when the peak pressure is chosen so that $S<=S_{crit}$, i.e. a peak pressure greater than that during the firing of the device. The peak pressure of the proof test is determined by the thickness and geometry of the glass being proof tested. Additionally, a factor is introduced to uplift the peak pressure to compensate for the small amount of crack growth which inevitably occurs during the second stage of the test. Typically, for the Intraject glass capsules, the peak pressure of the proof test is in the range 300-900 Bar, and more preferably 300-700 Bar, for example approximately 540 bar.

It has also been demonstrated at Weston Medical that a second successive two-stage proof test, of the type outlined above, with a peak pressure less than the peak pressure of the first proof test and greater than the peak pressure required to filter out flaws of size greater than $S_{crit}$, further reduces the breakage rate of the capsules during firing.

Figure 2:
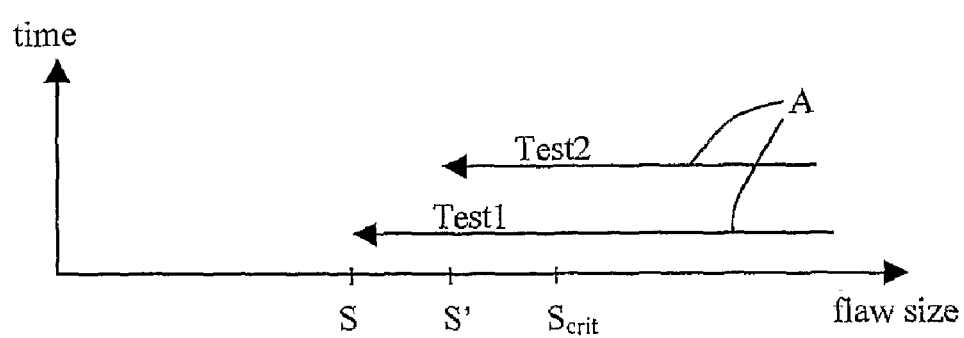
FIG. 2 shows how the method of the invention can be applied multiple times.

FIG. 2 shows this approach. The arrows A indicate the range of containers which will fail the respective test based on the maximum flaw size present.

At the end of the first proof test (Test1), the limited amount of crack growth which occurs during the second stage will have produced a batch of capsules in which there are a reduced number of capsules with flaw sizes above $S_{crit}$. During the first stage of the second proof test (Test2), all capsules in the batch with flaw sizes above S', where S' is between S and $S_{crit}$, will fail. During the second stage of the second proof test, when the pressure is reduced almost instantaneously to zero, inevitably, there will be some flaw growth in the batch of capsules; however, the probability of flaw growth is much reduced. The reason for this is that the majority of flaw growth only occurs in the very small number of capsules with flaws between S and S', i.e. the remaining capsules in which flaw growth occurred during the second stage of the first proof test. Since there will only be a small number of capsules in which the flaw sizes grew above S' during the second stage of the second proof test, the total number of capsules with flaw sizes above $S_{crit}$ will be a small number of a small number and hence the total number of capsules in the batch with flaw size above $S_{crit}$ will reduce. Further successive proof tests will also theoretically further reduce the number of capsules in the batch with flaw sizes above $S_{crit}$.

Figure 3:
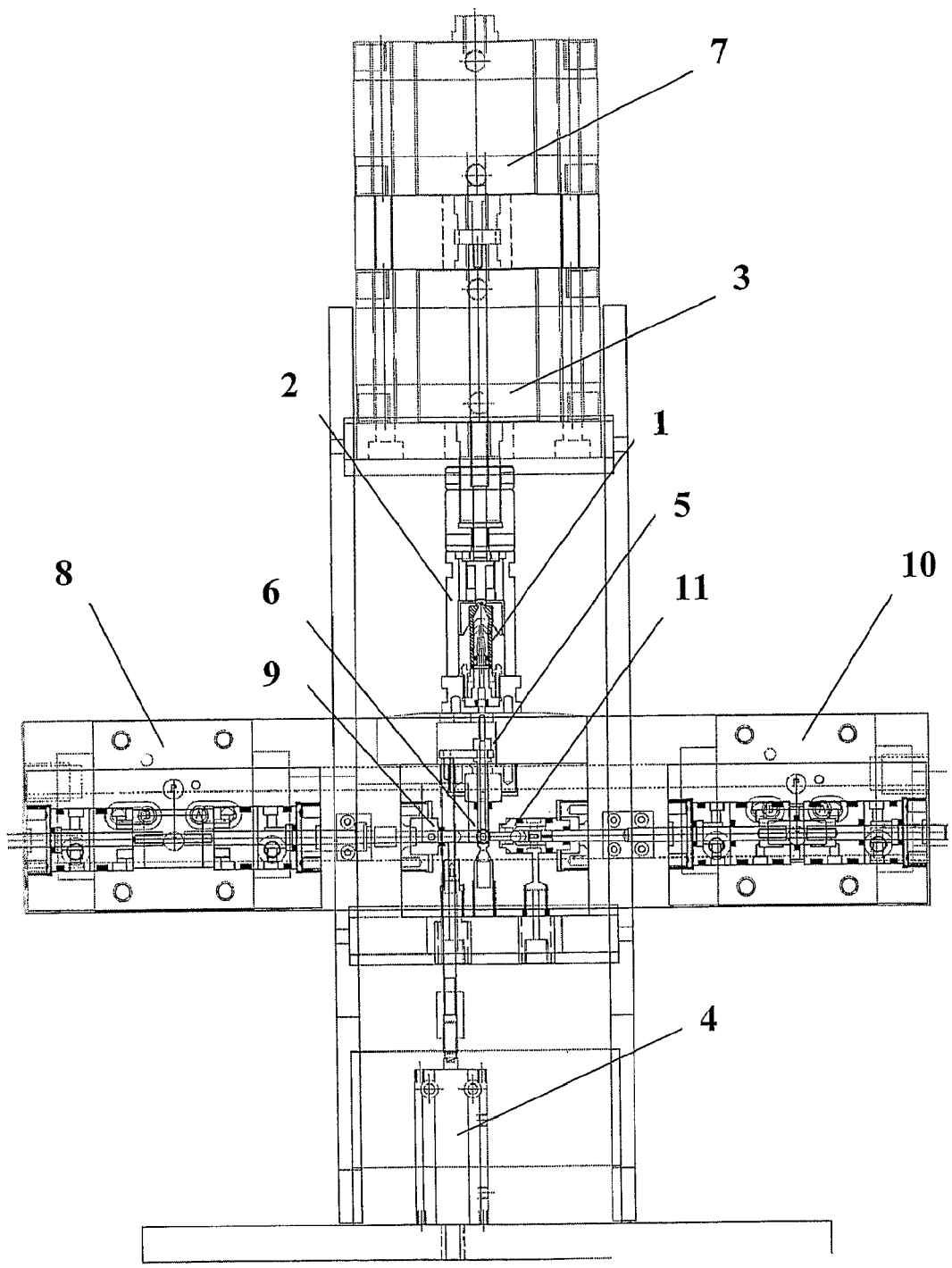
FIG. 3 illustrates a front profile of the mechanical test apparatus.

FIG. 3 presents an engineering diagram of the Weston Medical proof tester. Operation of the proof tester follows four discrete stages: Setting; Filling; Loading; and Unloading.

Setting

The glass capsule (1) is positioned into a test pot (2) which is subsequently loaded into position above the 'stinger' (5)—a sealed movable pipe that connects the high-pressure block (6) to the capsule test pot (2). The pot is clamped by a pneumatic actuator (3) and then the 'stinger' (5) is inserted into place by another pneumatic actuator (4). The high-pressure seals are then in place to prevent leaks from the 'stinger'.

Filling

A low-pressure system fills the volume of the high-pressure unit (6) with a liquid, usually water, and then the capsule (1) is filled with the same liquid through the 'stinger'

(5). The capsule (1) is then sealed by a valve at one end in the high-pressure unit and at the other end, at the top of the capsule, by a seal lowered by a third pneumatic actuator (7). The volume is also sealed by a ceramic ball held in place upon a seal (11) by a hydraulic valve (10). The volume of liquid in the capsule is ready to be pressurised.

Loading

A high speed hydraulic valve (8) drives a high quality piston through the high pressure seal (9) to increase the pressure in the capsule. Using the feedback from a high-speed piezoelectric pressure sensor, a high-speed processor controls the rate of increase in pressure as required.

Unloading

The system unloads the pressure in the capsule by actuating the other high-speed hydraulic valve (10) which then releases the ball-seal (11). With the ball free to move there is a near-instantaneous drop in pressure.

An alternative to this approach is to use a mechanical servo driven drive to load a liquid containing capsule via a sealing piston. The unloading cycle of the proof test is completed by a large pneumatic cylinder that, similar to the hydraulic system, is pressurized during the loading phase, and allows rapid release of the air during the unloading phase. The method has been demonstrated to be slightly slower than the hydraulic method disclosed above, but is almost equally effective.

Only one specific pressure profile has been given in FIG. 1. The duration of the different stages of the pressure profile and the pressures will of course be selected in dependence on the particular containers being tested, and the conditions to which the container is to be subsequently subjected. Suitable ranges for these time and pressure values have been given above and in the claims below.

The invention claimed is:

1. A method of testing the strength of a glass container, comprising:
   pressurizing the container, the container failing the test if it breaks;
   wherein the container is pressurized to be subjected to a pressure profile which in a first stage increases from a starting pressure to a peak pressure at a first average rate of pressure increase; and
   wherein in a second stage decreases from the peak pressure to the starting pressure at a second average rate of pressure decrease which is greater than the first average rate of pressure increase.

2. A method as claimed in claim 1, wherein the second stage of the pressure profile involves reducing the pressure substantially instantaneously to the starting pressure; and
   wherein the starting pressure is atmospheric pressure.

3. A method as claimed in claim 2, wherein the first stage of the pressure profile involved ramping the pressure substantially linearly to the peak pressure.

4. A method as claimed in claim 1, wherein pressurizing the container comprises filling the container with water and pressurizing the liquid; and
   wherein the pressure is applied by first sealing the container and applying the pressure hydrostatically using the water; and
   wherein the container seal is applied using an o-ring which seals under hydrostatic pressure.

5. A method as claimed in claim 4, wherein the pressure is released in the second stage by opening a hydraulic valve.

6. A method as claimed in claim 4, wherein the pressure is applied using a mechanical servo driven drive and the pressure is released in the second stage by a pneumatic cylinder.

7. A method as claimed in claim 1, wherein the container is subjected to a plurality of tests.

8. A method as claimed in claim 1, wherein the first stage of the pressure profile has a duration of 30-250 ms; and
   wherein the second stage of the pressure profile has a duration of 1-10 ms.

9. A method as claimed in claim 8, wherein the first stage of the pressure profile has a duration of 40-70 ms; and
   wherein the second stage of the pressure profile has a duration of 0-2 ms.

10. A method as claimed in claim 1, wherein the second stage immediately follows the first stage.

11. A method as claimed in claim 1, wherein the peak pressure is in the range 300-900 Bar.

12. A method as claimed in claim 11, wherein the peak pressure is in the range 300-700 Bar.

13. A method as claimed in any one of claims 1, 2, 3, 4, 7 and 10, wherein the pressure to which the container is controlled using feedback from a pressure sensor.

14. A method as claimed in claim 13, wherein the container comprises a glass capsule for a needle-less injector.

15. A method of testing the strength of a glass container, comprising:
   pressurizing the container, the container failing the test if it breaks;
   wherein the container is pressurized and subjected to a pressure profile which in a first stage increases from a starting pressure to a peak pressure at a first average rate of pressure increase over a first period of time of 30-250 ms; and
   wherein in a second stage which immediately follows the first stage and decreases from the peak pressure to the starting pressure at a second average rate of pressure decrease over a second period of time of 0-10 ms.

16. A method as claimed in claim 15, wherein the second period of time is substantially instantaneous; and
   wherein the starting pressure is atmospheric pressure.

17. A method as claimed in claim 16, wherein the first stage of the pressure profile involved ramping the pressure substantially linearly to the peak pressure.

18. A method as claimed in claim 15, wherein the first period of time has a duration of 40-70 ms.

19. A method as claimed in claim 18, wherein the second period of time has a duration of 0-2 ms.

20. A method as claimed in claim 19, wherein the container comprises a glass capsule for a needle-less injector.

21. A method as claimed in claim 15, wherein the peak pressure is in the range 300-900 Bar.

22. A method as claimed in claim 15, wherein the peak pressure is in the range 300-700 Bar.

* * * * *